United States Patent [19]

Nosé et al.

[11] Patent Number: 5,399,074
[45] Date of Patent: Mar. 21, 1995

[54] MOTOR DRIVEN SEALLESS BLOOD PUMP

[75] Inventors: Yukihiko Nosé; Setsuo Takatani, both of Houston, Tex.; Ichiro Sakuma, Tsurugashima, Japan

[73] Assignee: Kyocera Corporation, Kyoto, Japan

[21] Appl. No.: 940,520

[22] Filed: Sep. 4, 1992

[51] Int. Cl.$^6$ .................. F04B 17/00; F04B 15/02
[52] U.S. Cl. .................. 417/423.1; 417/423.7; 417/423.12; 417/423.14; 415/900; 416/3
[58] Field of Search .......... 417/410 R, 423.1, 423.7, 417/423.11, 423.12, 423.14, 423.15, 424.1; 415/900, 122.1; 604/151; 416/3

[56] References Cited

U.S. PATENT DOCUMENTS

| | | | |
|---|---|---|---|
| 4,135,253 | 1/1979 | Reich et al. | 415/900 |
| 4,507,048 | 3/1985 | Belenger et al. | 415/900 |
| 4,818,193 | 4/1989 | Laing et al. | 417/423.14 |
| 4,850,818 | 7/1989 | Kotera | 417/423.14 |
| 4,984,972 | 1/1991 | Clausen et al. | 415/900 |
| 4,994,078 | 2/1991 | Javik | 415/900 |
| 5,049,134 | 9/1991 | Golding et al. | 417/423.1 |
| 5,055,005 | 10/1981 | Kletschka | 415/900 |

FOREIGN PATENT DOCUMENTS

1434226  5/1976  United Kingdom ........... 417/423.14

OTHER PUBLICATIONS

"Development of a Motor Driven Seal-Less Centrifugal Blood Pump", Int'l Workshop on Rotary Blood Pumps, I. Sakuma, et al., Sep. 1991, pp. 48–53.

"Artifical Organs", *Official Journal of the Int'l Society for Artificial Organs*, Aug. 1991, vol. 15, No. 4, pp. 258 and 316.

"1992 Abstracts", *American Society for Artificial Internal Organs*, May 7–9, 1992, p. 45.

*Primary Examiner*—Richard A. Bertsch
*Assistant Examiner*—Roland G. McAndrews
*Attorney, Agent, or Firm*—Spensley Horn Jubas & Lubitz

[57] ABSTRACT

A centrifugal blood pump, used for heart-lung machines or the like, comprises an impeller, a casing having a suction inlet and a delivery outlet and being equipped with a space for rotatably accommodating the impeller, and a magnetic drive means disposed outside the casing. The impeller is of a rotationally symmetric shape and has a rotary vane section and a cylindrical section equipped with a magnet means. The magnet drive means for generating a rotating magnetic field coaxially encloses the magnet means of the above-mentioned cylindrical section and rotates the impeller in cooperation with the magnet means. At least the end section of the impeller's rotation center on the rotary vane section side is supported preferably by a pivot bearing. The pivot and the bearing thereof are preferably made of ceramics.

16 Claims, 6 Drawing Sheets

MOTOR DRIVEN SEALLESS BLOOD PUMP

BACKGROUND OF THE INVENTION

1. Field of the Invention

The present invention relates to a centrifugal blood pump used For heart-lung machines or the like.

2. Prior Arts

Conventionally, pulsatile pumps and roller pumps were used as blood circulation pumps for heart-lung machines or the like. In recent years, centrifugal pumps which are compact, efficient and reliable have become to be used widely.

However, centrifugal blood pumps are apt to cause the problem of generating thrombi at bearings and sealing parts because of blood stagnation around the sealing parts for sealing the rotation axis of the impeller with vanes and heat generation in the sealing parts. In addition, there is the danger of leaking blood through the sealing parts. Because of these problems, the pumps cannot be operated continuously for an extended period of time.

To solve these problems, various centrifugal blood pumps have been proposed, which require no seals for the rotation shaft.

In the case of the blood pump described in the specification of U.S. Pat No. 4,688,988, the impeller with vanes accommodated in the casing of the pump is equipped with magnets which form a part of a magnetic suspension means and magnets which form a part of a magnetic rotation means. Outside the casing, the pump is equipped with an electric magnet means disposed corresponding to the magnets of the impeller. By operating these electric magnet means, the impeller in the casing is suspended in the normal position and rotated properly. With this type of pump, however, it is difficult to control the position and suspension conditions of the impeller with vanes, causing unstable impeller rotation. Furthermore, the pump becomes complicated and large, confronting difficulty when it is put to practical use.

In the case of the blood pump described in the specification of U.S. Pat. No. 4,984,972, the boss located in the center of the impeller is mounted on the bearing supported in the pump chamber inside the housing of the disposable pumping unit of the pump, for example, the bearing formed at the top section of the conical stator of the pump, to support the impeller, and the magnets disposed around the impeller are combined magnetically to rotate the impeller and the magnetic drive means disposed outside the pumping unit. Since the impeller of this pump is supported only at a single point and the magnets are carried on the impeller, it is difficult to balance the impeller, causing unstable rotation.

In the case of the centrifugal blood pump described in the specification of U.S. Pat. No. 4,507,048, the nearly conical impeller with vanes of the pump, rotatably accommodated in the casing, is supported by the watch-type jewelled pivots formed at the upper and lower ends of the center axis thereof. On the bottom surface side of the conical impeller, a magnetic means is disposed and cooperates with the magnetic drive means disposed outside the casing to rotate the impeller. Since the center axis of the impeller of this pump is supported by the two upper and lower jewelled pivots, the impeller's dynamic balance of the pump is better than that of the pump described in the above-mentioned U.S. Pat. No. 4,984,972, ensuring stable rotation of the impeller.

However, since this pump has magnets on the bottom surface of the conical impeller, it is necessary to reduce the gap between the bottom surface of the impeller and the casing to enhance the efficiency of impeller rotation obtained by the cooperation of the magnets and the magnet drive means outside the casing. As a result of reducing the gap, it is difficult for blood to flow through the gap, thereby being apt to cause a problem of generation of thrombi, particularly at the jewelled pivot on the bottom surface side of the impeller.

As described above, the centrifugal blood pumps having been proposed so far without using shut-off seals had various problems and could not be put to practical use.

SUMMARY OF THE INVENTION

The present invention is intended to solve the above-mentioned problems encountered in centrifugal blood pumps. An object of the present invention is to provide a centrifugal blood pump having no seals on its rotation axis and capable of stably rotating an impeller with vanes, thereby scarcely generating thrombi.

Another object of the present invention is to provide a centrifugal blood pump which scarcely causes hemolysis.

A further object of the present invention is to provide a centrifugal blood pump which scarcely generates thrombi or hemolysis and is capable of being operated for an extended period of time.

To achieve the above-mentioned objects, the blood pump provided by the present invention comprises a casing having a suction inlet and a delivery outlet, an impeller of a rotationally symmetric shape which is encased in the casing, and a magnet drive means disposed outside the casing coaxially to the impeller, the impeller having a rotary vane section on the outlet side and a cylindrical section equipped with a magnet means on the suction side away from the rotary vane section, and the magnet drive means being positioned so as to enclose the magnet means with the casing interposed therebetween in order to rotate the impeller around the rotation center thereof in cooperation with the magnet means, wherein at least the end section of the impeller's rotation center on the rotary vane section side is supported by a bearing.

DETAILED DESCRIPTION OF THE INVENTION

Figure 1:
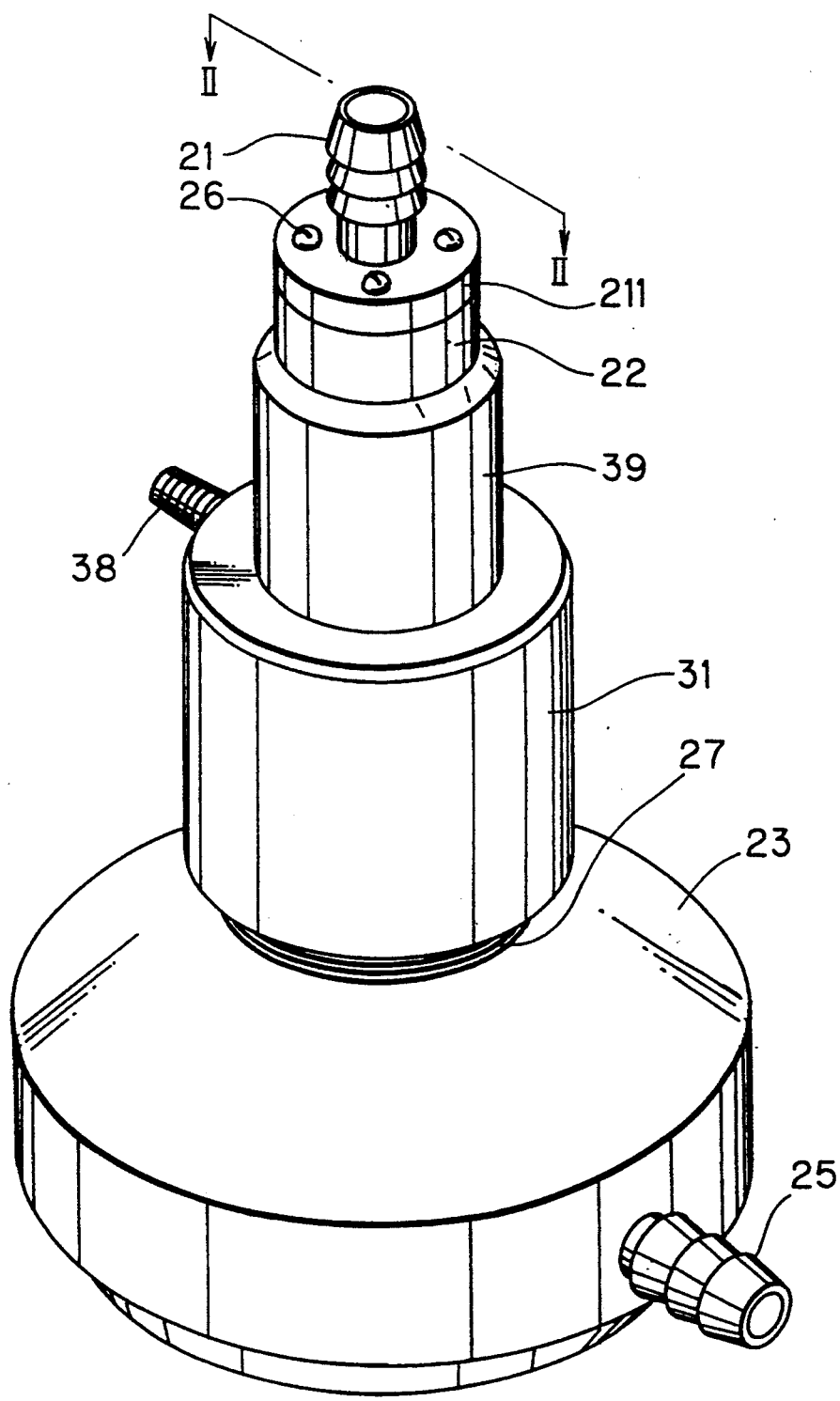
FIG. 1 is an external perspective view of an embodiment of the blood pump of the present invention.

The present invention relates to a novel centrifugal blood pump comprising a casing having a suction inlet and a delivery outlet, an impeller of a rotationally symmetric shape which is encased in the casing, and a magnet drive means disposed outside the casing coaxially to the impeller. The impeller has a rotary vane section equipped with pump vanes on the external surface thereof and a cylindrical section located on the suction inlet side away from the rotary vane section. The cylindrical section is equipped with a magnet means such as permanent magnets to magnetically rotate the impeller around the rotation center (axis) thereof in cooperation with the above-mentioned magnet drive means. The magnetic drive means is located to coaxially enclose the magnetic means of the cylindrical section of the impeller with the casing interposed therebetween. The impeller is supported by a bearing at the end of the impeller's rotation center at least on the rotary vane section side. In the preferred embodiment of the present invention, the end of the impeller's rotation center on the rotary vane section side is supported by a pivot and a pivot bearing. Both the pivot and pivot bearing included in the pivot-bearing combination are preferably made of ceramics.

When the rotationally symmetric impeller is rotated around the center thereof, the impeller rotates stably and self-supportingly around the lower end of the rotation center by the gyroscopic function. The impeller is mainly supported by the bearing on the lower section side, that is, on the rotary vane section side and no large load is applied to the bearing on the upper section side. It is thus possible to omit the bearing at the end section of the impeller's s rotation center on the impeller's top section side. However, the bearing used to support the end section can allow the impeller to rotate more stably. Either a contact-type bearing, such as a pivot bearing or a journal bearing, or a non-contact-type bearing, such as a magnet bearing, can be used as the bearing used at the upper end section. As the bearing used on the lower section side, a pivot-bearing unit can be used advantageously since the load in the radial direction of the impeller is reduced by the gyroscopic function.

The rotation of the impeller of the present invention's blood pump is further stabilized since the magnetic means and the magnetic drive means for magnetically rotating the impeller are arranged coaxially in such a manner as the relationship between the rotor and stator of a motor. In addition to the above-mentioned gyroscopic function and the coaxial arrangement of the magnetic means and the magnetic drive means, by preferably supporting the rotation center of the impeller at both the upper and lower ends of the rotation center, the rotation of the impeller can be maintained more stably As a result, no irregular or excessive force is applied to the rotation center support sections of the impeller, thereby scarcely causing blood cell damage, that is, hemolysis.

With the blood pump of the present invention, the magnetic means mounted on the impeller is positioned at the cylindrical section on the suction inlet side, instead of the position on the rotary vane section side of the impeller, thereby allowing blood to smoothly flow through the gap between the impeller and the casing. For this reason, thrombi are rarely generated, even if the gap between the casing and the impeller's cylindrical section equipped with magnetic means such as permanent magnets is made small to increase the drive power and efficiency of the magnetic drive operation of the impeller. In other words, the blood pump of the present invention can prevent the generation of thrombi while maintaining the high efficiency of the magnetic drive operation.

Furthermore, since the magnetic means of the present invention is provided on the cylindrical section of the impeller instead of the position on the bottom surface side of the impeller, the gap between the bottom surface of the impeller and the bottom surface of the casing opposite thereto can be made relatively large. Accordingly, blood stagnation and excessive agitation do not occur at this gap, thereby scarcely generating thrombi and hemolysis at the pivot-bearing units or other parts. Auxiliary vanes or the like can be provided on the bottom surface of the impeller as required to enhance the flow of blood from the gap to the delivery outlet, avoiding blood stagnation at this portion. Consequently, the blood pump of the present invention scarcely generates thrombi and hemolysis and can thus be operated for an extended period of time.

The structural details and the resulting advantages of the blood pump of the present invention will be apparent from the following description of the preferred embodiments, referring to the accompanying drawings.

DETAILED DESCRIPTION OF THE PREFERRED EMBODIMENTS

Figure 2:
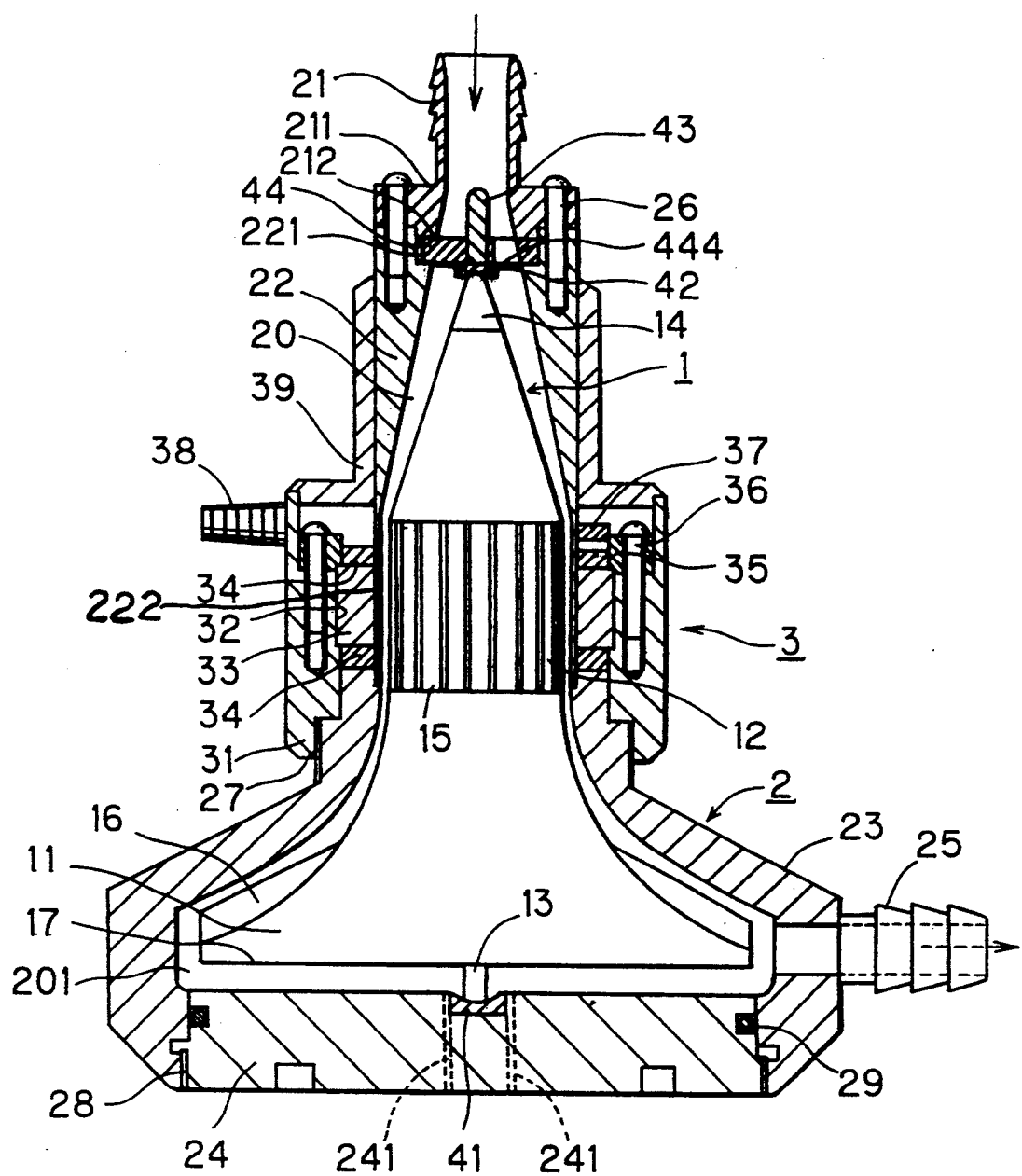
FIG. 2 is a sectional view taken along line II—II of FIG. 1.

FIGS. 1 and 2 show an embodiment of the centrifugal blood pump of the present invention. Numeral 1 represents an impeller rotatably accommodated in a casing 2 and having a rotationally symmetric shape. The impeller 1 is made of plastic material for example and has a rotary vane section 11 located at the impeller's lower section and a cylindrical section 12 located on the side of the suction inlet 21 away from the rotary vane section 11. At the bottom surface 17 of the impeller, a pivot 13 is disposed so that its center line aligns with the rotation center of the impeller. Also, a pivot 14 is embedded in the top section of the impeller such that the center line of the pivot aligns with the rotation center of the impeller. As the magnetic means, a group of permanent magnets 15 are arranged symmetrically along the periphery of the cylindrical section 12. Numeral 16 represents each vane. A plurality of vanes 16 are used to transfer blood to a delivery outlet 25 by impeller rotation, thereby discharging blood From the delivery outlet 25. The cylindrical section 12 is not required to have a complete cylindrical shape, but may have a slightly tapered shape.

Figure 5:
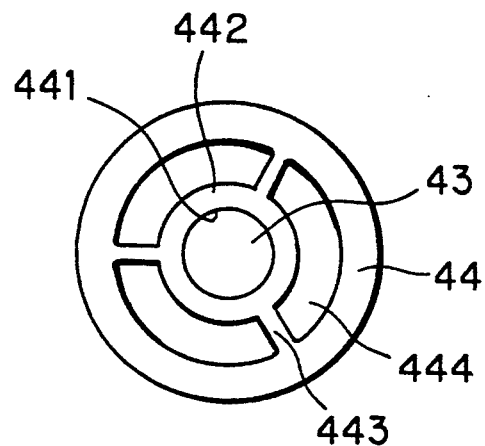
FIG. 5 is a plan view of the support section of a holding rod joined with a pivot bearing

The casing 2 made of plastic material or the like comprises the suction inlet 21, an upper casing 22, a side casing 23 and a bottom plate 24, and rotatably accommodates the impeller 1 in the space 20 thereof. At the top section of the upper casing 22, the flange 211 of the suction inlet 21 is secured by screws 26. In addition, at the top section of the upper casing 22, an annular recessed section 221 is formed. In the recessed section 221, a support ring 44 made of plastic material or the like is installed and pressed by the holding surface 212 of the Flange 211 to ensure hermetical sealing between the upper casing 22 and the flange 211. The holding Pod 43 joined with the bearing 42 of the pivot 14 by using an appropriate means such as adhesive is inserted into the hole 441 of the center ring 442 supported by the rib 443 of the support ring 44 and is supported by the support ring 44 as shown in FIG. 5. The blood supplied through the suction inlet 21 passes through the hole 444 of the support ring 44 and flows into the space 20 between the upper casing 22 and the impeller 1.

The cylindrical section 222 at the lower section of the upper casing 22 is made thinner than other sections to reduce the gap between the permanent magnets 15 and a coil 34 described later. The lower end section of the upper casing 22 is hermetically connected to the upper end section of the side casing 23 by an appropriate method such as welding. To the inner surface of the side casing 23 on the lower end side thereof, the bottom plate 24 is secured by a screw 28 so that the bearing 41 embedded in the center of the upper surface of the bottom plate 24 can properly contact the pivot 15, so that the pivot 14 can properly contact the bearing 42 and so that the bottom plate 24 can be positioned vertically by screwing movement. Numeral 29 represents an O-ring used to hermetically seal the connection of the side casing 22 and the bottom plate 24. The side casing 23 has the delivery outlet 25 just above the connection section of the side casing 23 and the bottom plate 24. The delivery outlet 25 is disposed to extend in the direction tangential or nearly tangential to the rotation direction of the impeller 1 and on the tangential side of the rotation direction.

The magnetic drive means 3 disposed outside the casing 2 is described below. In the inner surface of the side wall 31 contacted to the side casing 23 by a screw 27, a magnetic core 33 with the coil 34 wound thereon is fitted in the annular recessed section 32 disposed coaxially to the cylindrical section 222 of the upper casing 22. The magnetic core 33 is secured and fixed via a holding member 35 by screws 36. The coil 34 and the magnetic core 33 are disposed so that they nearly contact the cylindrical section 222 of the casing 22. With this structure, the coil 34 coaxially encloses the permanent magnets 15 installed in the impeller 1 so that the thin cylindrical section 222 of the upper casing 22 is interposed therebetween. When the coil 34 is actuated, the impeller 1 is rotated by the mutual action of the coil 34 for generating a rotating magnetic field and the permanent magnets 15. The magnetic drive means 3 and the impeller's cylindrical section 12 equipped with the magnetic means may be the stator and rotor of a brushless DC motor respectively.

According to the results of the experiments conducted by the inventors of the present invention, the gap between the cylindrical section 222 of the casing 22 and the impeller's cylindrical section 12 equipped with the permanent magnets 15 is preferably determined in the range of 0.5 to 3.0 mm. If the gap is smaller than 0.5 mm, thrombi are apt to be generated and pressure loss increases. If the gap exceeds 3.0 mm, magnetic drive force and the efficiency of the pump decrease. Even when the above-mentioned gap exceeds 3 mm, sufficient drive force can be obtained if the magnetic force generated by the coil 34 is made greater. In this case, however, the coil 34 must be made larger.

Figure 9:
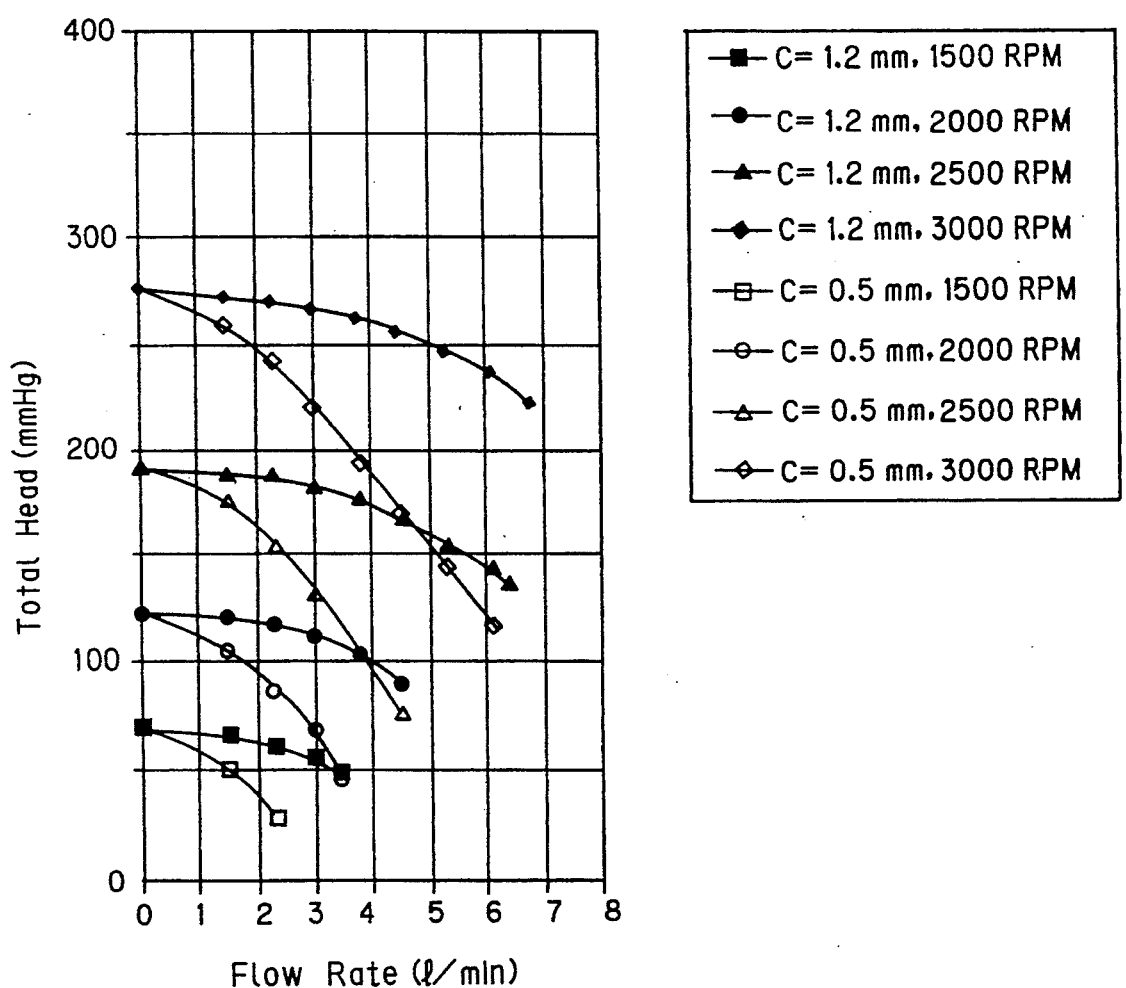
FIG. 9 is a graph illustrating the performance curve of the blood pump of the present invention.

FIG. 9 shows the relationship between the flow rate of blood and the delivery pressure in the case of the blood pump of the present invention at various rotation speeds, with the above-mentioned gap C set at 0.5 or 1.2 mm. According to this graph, it is understood that the blood pump of the present invention has a sufficient capability for transferring blood by pressure.

As the magnetic drive means, a group of permanent magnets can be arranged, disposed and rotated by a motor, instead of generating a rotating magnetic field using a coil. In this case, the abovementioned gap is preferably in the range of 0.5 to 10 mm, since strong magnets can be used for the permanent magnets arranged and disposed outside the casing. With the blood pump of the present invention, the unit comprising the casing 2 and the impeller 1 is made disposable and the magnetic drive means 3 is used repeatedly. It is therefore advantageous that the permanent magnets arranged and disposed outside the casing are composed of strong magnets and that the permanent magnets mounted on the impeller are composed of cheap magnets. The magnetic drive means incorporating permanent magnets, instead of the coil 34, can be provided as an auxiliary magnetic drive means in case of power failure, since the permanent magnets can be rotated by hand.

Referring to FIG. 2, numeral 37 represents a Hall sensor used to detect the gap between the impeller's permanent magnets and the casing, and the position and the rotation speed of the impeller. Numeral 38 represents the input/output ports for lead wires (not shown). Numeral 39 represents a cover set in or secured by screws to the upper end of the side wall 31 of the magnetic drive means 3. Since the disposable unit comprising the casing 2 and the impeller 1 is connected to the magnetic drive means 3 only by the screw 27, the disposable unit can be attached to or detached from the magnetic drive means 3 by engaging or disengaging the screw 27.

Figure 4:
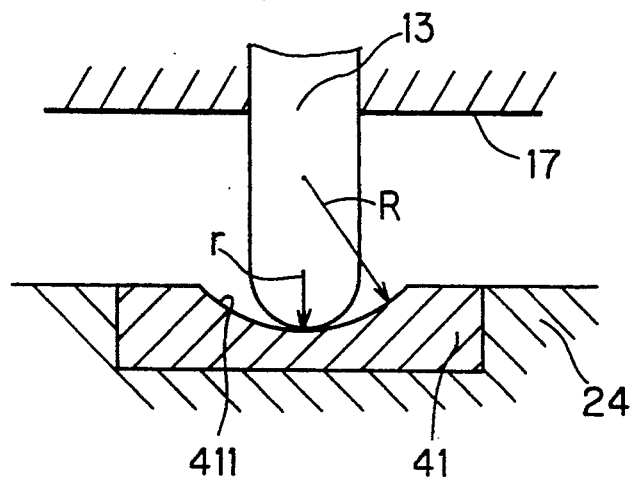
FIG. 4 is an enlarged sectional view of a pivot bearing.

According to the experiments, conducted by the inventors of the present invention, regarding the pivot 13 and the bearing 41 thereof located on the lower section side of the impeller and the pivot 14 and the bearing 42 thereof located on the upper section side of the impeller, ceramics are superior to metals and plastic materials in resistance against thrombus generation and thus rarely generate thrombi. In addition, ceramics are highly resistant against friction. For these reasons, at least the pivot or the bearing of each of these pivot-bearing combinations is desired to be made of ceramics such as alumina, zirconia, silicon carbide or silicon nitride. In particular, since silicon carbide is high in heat conductivity, it is apt to easily dissipate friction heat. Furthermore, since silicon carbide contains carbon, it is superior in sliding performance. For these reasons, silicon carbide is best suited. Alumina is also suited for practical applications since it is low in cost and relatively high in heat conductivity. Regarding the radius of curvature r at the leading end of the pivot 13 and the radius of curvature R at the recessed curved surface 411 of the bearing 41 as shown in FIG. 4, the ratio of R/r is preferred in the range of 1 to 4. If the ratio exceeds 4, the support of the pivot by the bearing becomes unstable. The range of 2 to 4 is further desirable, since it has been confirmed by experiments that hemolysis occurs far scarcely when the ratio is 2 or more.

As described above, since no large load is applied to the end section of the impeller's rotation center on the impeller's top section side because of the gyroscopic function, the bearing used at the end section is not limited to a pivot bearing, but a variety of types of bearings including non-contact-type bearings can be used suitably. In some cases, the impeller can be used without being supported by the bearing at the top end section. Although in the pump as shown in FIG. 2 at the end section of the impeller's rotation center on the impeller's top section side and on the rotary vane side, pivots 14 and 13 are embedded in the impeller, it is of course possible that the rotation center can have a shape of a single shaft extending from the top end to the lower end.

Figure 8:
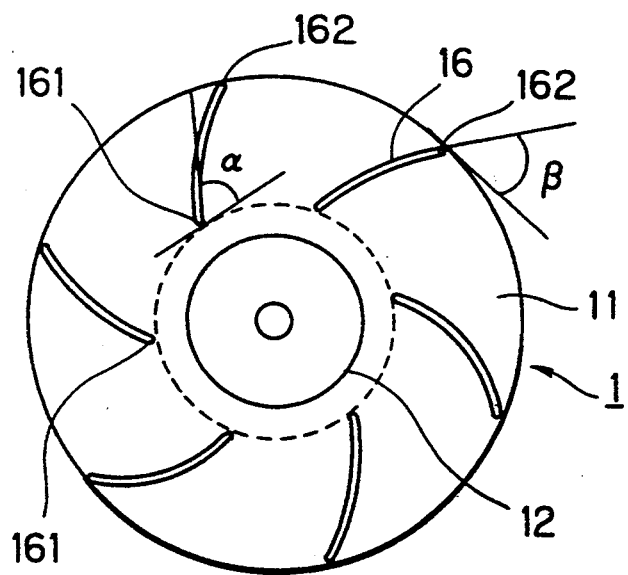
FIG. 8 is a plan view of the impeller illustrating the entrance and exit angles of the impeller's vanes.

The vanes 16 of the impeller 1 can have a variety of shapes, such as a curved or straight shape, as long as the vanes offer pumping functions. However, according to the results of the experiments conducted by the inventors of the present invention, hemolysis occurs far scarcely when the entrance angle α of the vane is in the range of 10 to 70 degrees and the exit angle β of the vane is in the range of 50 to 70 degrees. It is therefore desirable to determine the entrance and exit angles of the vane in the abovementioned ranges. As shown in FIG. 8 (indicating curved vanes), the above-mentioned entrance angle α is an angle formed by the tangent line of the circle obtained by connecting the leading ends 161 of the vanes 16 on the blood entrance sides and the tangent line at the blood entrance end of each vane, and the above-mentioned exit angle β is an angle formed by the tangent line at the blood exit end 162 of each vane and the tangent line of the external circle of the impeller's lower end section at the exit end 162 of each vane.

Figure 3:
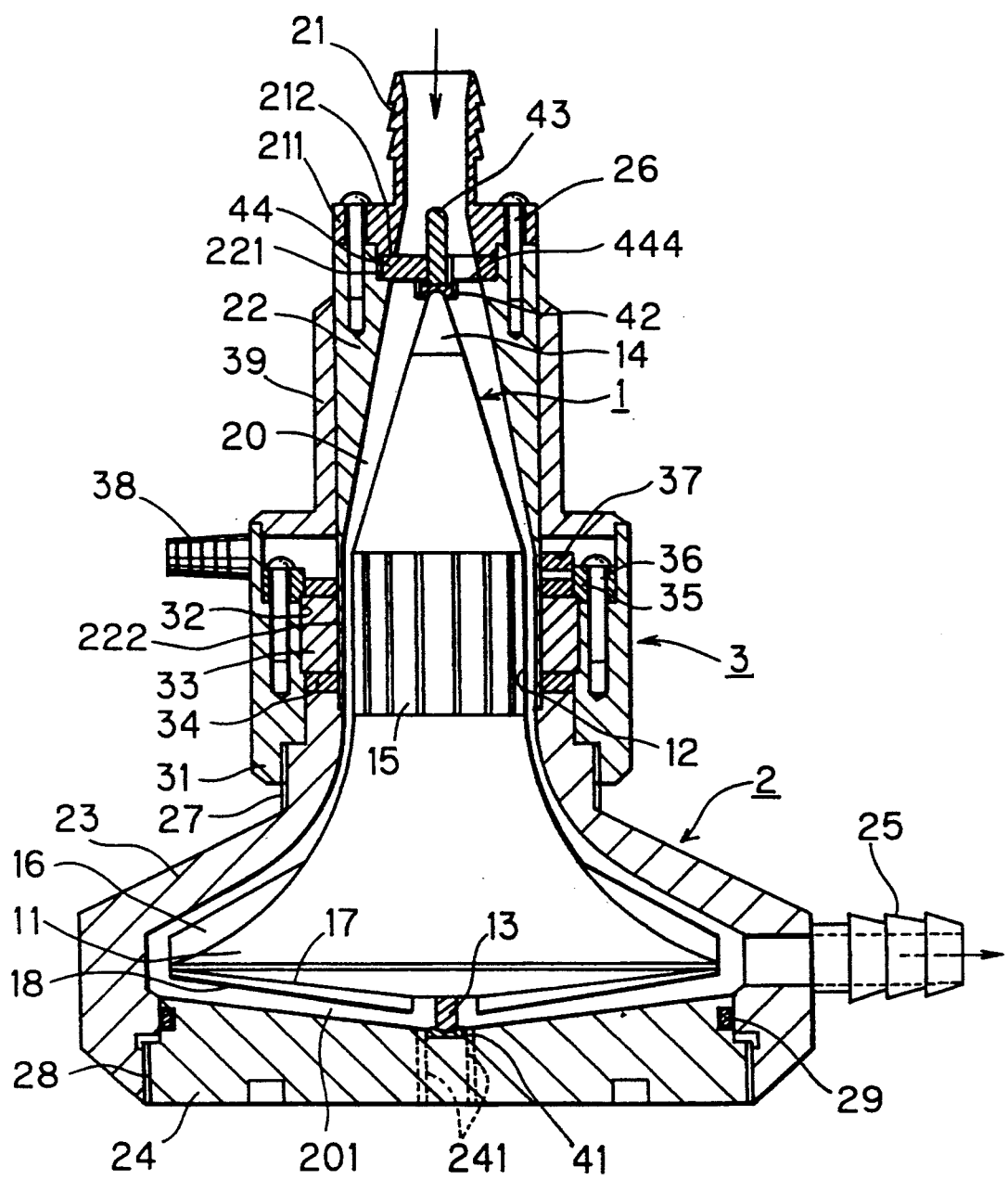
FIG. 3 is a longitudinal sectional view of another embodiment of the blood pump of the present invention.
Figure 6:
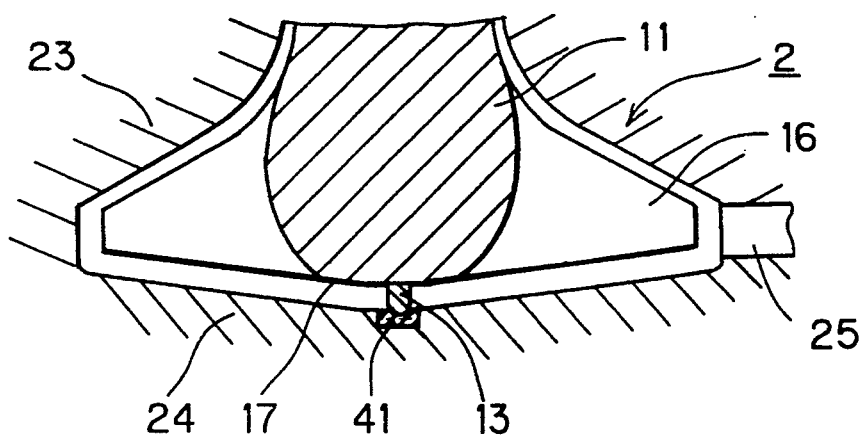
FIGS. 6 and 7 are sectional views illustrating other structures of the rotary vane section of the impeller.
Figure 7:
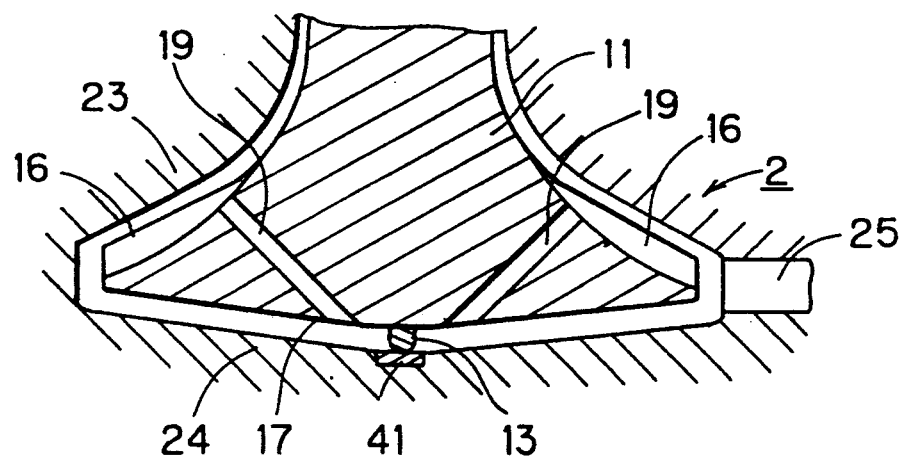

With the present invention, auxiliary vanes can be provided on the bottom surface 17 of the impeller 1 to allow the blood flowed into the space 201 between the bottom surface 17 of the impeller 1 and the casing 2 to be transferred to the delivery outlet 25, and to eliminate stagnation in the space, thereby preventing the generation of thrombi. FIG. 3 shows the cross section of an embodiment equipped with such auxiliary vanes. The generation of thrombi can further be prevented by providing water purging through holes 241 around the bearing 41 of the bottom plate 24 as shown by the broken lines in FIG. 3 and supplying a mixture liquid from the outside comprising a physiological saline solution and a blood anti-coagulation agent or a thrombus dissolution agent. More suitable results are obtained by providing porous elements inside the through holes 241 so that the supplied liquid can seep through the porous elements, or by forming the bearing 41 by using a porous element having lots of micro pores with the sizes ranging from 60 Å to several millimeters so that the supplied liquid can seep through the bearing 41. The same reference numerals used in FIGS. 2 and 3 represent the same corresponding elements. The embodiment shown in FIG. 3 is the same as that shown in FIG. 2 except for the shapes of the bottom surface 17 of the impeller 1 and the bottom plate 24 of the casing 2 and except that the auxiliary vanes 18 and the water purging through holes 241 are provided. FIGS. 6 and 7 show embodiments which enhance the flow of the blood located in the space between the bottom surface 17 of the impeller 1 and the bottom plate 24 of the casing 2 to prevent the generation of thrombi. The rotary vane section 11 shown in FIG. 6 is an open type. The rotary vane section 11 shown in FIG. 7 is equipped with through holes 19 which pass from the external surface of the rotary vane section 11 to positions close to the pivot 13 of the bottom surface 17.

Although the present invention has been described with reference to preferred embodiments, a man skilled in the art will recognize that changes may be made in form and detail without departing from the spirit and scope of the invention.

We claim:

1. A blood pump comprising a casing having a suction side provided with a suction inlet and an outlet side provided with a delivery outlet, an impeller of a rotationally symmetric shape which is encased in the casing, and a magnet drive means disposed outside the casing coaxially to said impeller, said impeller having a rotary vane section on the outlet side and a cylindrical section equipped with a magnet means on the suction side away from the rotary vane section, and said magnet drive means being positioned so as to enclose the magnet means with the casing interposed therebetween in order to rotate the impeller around the rotation center thereof in cooperation with the magnet means, wherein the impeller is supported at the outlet side by a pivot and a pivot bearing.

2. A blood pump according to claim 1, wherein the impeller is supported at the suction side by a contact-type bearing.

3. A blood pump according to claim 1, wherein the impeller is supported at the suction side by a non-contact-type bearing.

4. A blood pump according to claim 1, wherein said pivot is made of ceramics.

5. A blood pump according to claim 4, wherein said rotary vane section of said impeller has a surface which faces said pivot and pivot bearing, and said impeller further comprises vanes on said surface of said impeller.

6. A blood pump according to claim 1 or 4, wherein the ratio of the radius of curvature r of the leading end of said pivot to the radius of curvature R of the recessed curved surface of said bearing is in the range of 1 to 4.

7. A blood pump according to claim 1, or 4, wherein said magnetic means is composed of permanent magnets, said magnetic drive means is composed of an electric coil for generating a rotating magnetic field, and the gap between said cylindrical section equipped with said magnetic means and said casing opposite thereto is in the range of 0.5 to 3.0 mm.

8. A blood pump according to claim 1 or 5, wherein said magnet means and said magnet drive means are composed of permanent magnets, and the gap between said cylindrical section equipped with said magnet means and said casing opposite thereto is in the range of 0.5 to 10.0 mm.

9. A blood pump according to claim 1 or 4, wherein the casing forms a chamber containing the impeller and communicating with the delivery outlet, and through holes passing between said chamber and the outside of said casing are provided at positions around said bearing for supporting the end section of the impeller's rotation center on the rotary vane section side.

10. A blood pump according to claim 1 wherein said pivot bearing is made of ceramics.

11. A blood pump according to claim 10, wherein the ratio of the radius of curvature R of the leading end of said pivot to the radius of curvature R of the recessed curved surface of said bearing is in the range of 1 to 4.

12. A blood pump according to claim 10, wherein said magnetic means is composed of permanent magnets, said magnetic drive means is composed of an electric coil for generating a rotating magnetic field, and the gap between said cylindrical section equipped with said magnetic means and said casing opposite thereto is in the range of 0.5 to 3.0 mm.

13. A blood pump according to claim 10, wherein said magnet means and said magnet drive means are composed of permanent magnets, and the gap between said cylindrical section equipped with said magnet means and said casing opposite thereto is in the range of 0.5 to 10.0 mm.

14. A blood pump according to claim 10 wherein the casing forms a chamber containing the impeller and communicating with the delivery outlet, and through holes passing between said chamber and the outside of said casing are provided at positions around said bearing for supporting the end section of the impeller's rotation center on the rotary vane section side.

15. A blood pump according to claim 10, wherein said rotary vane section of said impeller has a surface which faces said pivot and pivot bearing, and said impeller further comprises vanes on said surface of said impeller.

16. A blood pump comprising a casing having a suction side provided with a suction inlet and an outlet side provided with a delivery outlet, an impeller of a rotationally symmetric shape which is encased in the casing, and a magnet drive means disposed outside the casing coaxially to said impeller, said impeller having a rotary vane section on the outlet side and a cylindrical section equipped with a magnet means on the suction side away from the rotary vane section, and said magnet drive means being positioned so as to enclose the magnet means with the casing interposed therebetween in order to rotate the impeller around the rotation center thereof in cooperation with the magnet means, wherein the impeller is supported at the outlet side by a bearing, the casing forms a chamber containing the impeller and communicating with the delivery outlet, and through holes passing between said chamber and the outside of said casing are provided at positions around said bearing for supporting the end section of the impeller's rotation center on the rotary vane section side.

* * * * *

UNITED STATES PATENT AND TRADEMARK OFFICE
CERTIFICATE OF CORRECTION

PATENT NO. : 5,399,074
DATED : March 21, 1995
INVENTOR(S) : Nose et al.

It is certified that error appears in the above-indentified patent and that said Letters Patent is hereby corrected as shown below:

On the title page, under [21] Appl. No. : the correct Serial No. is --940,510--.

Signed and Sealed this

Sixth Day of June, 1995

Attest:

BRUCE LEHMAN

Attesting Officer     Commissioner of Patents and Trademarks